United States Patent
Tomiyama et al.

(10) Patent No.: US 11,583,494 B2
(45) Date of Patent: Feb. 21, 2023

(54) PHARMACEUTICAL COMPOSITION FOR NASAL ADMINISTRATION

(71) Applicant: MEDILABO RFP, INC., Tokyo (JP)

(72) Inventors: Takami Tomiyama, Osaka (JP); Tomohiro Umeda, Osaka (JP)

(73) Assignee: MEDILABO RFP, INC., Tokyo (JP)

( * ) Notice: Subject to any disclaimer, the term of this patent is extended or adjusted under 35 U.S.C. 154(b) by 159 days.

(21) Appl. No.: 16/628,476

(22) PCT Filed: Jul. 5, 2018

(86) PCT No.: PCT/JP2018/025512
§ 371 (c)(1),
(2) Date: Jan. 3, 2020

(87) PCT Pub. No.: WO2019/009359
PCT Pub. Date: Jan. 10, 2019

(65) Prior Publication Data
US 2020/0129426 A1    Apr. 30, 2020

(30) Foreign Application Priority Data
Jul. 6, 2017 (JP) .............................. JP2017-132955

(51) Int. Cl.
*A61K 9/10* (2006.01)
*A61K 9/00* (2006.01)
*A61P 25/28* (2006.01)
*A61K 31/496* (2006.01)

(52) U.S. Cl.
CPC .............. *A61K 9/0043* (2013.01); *A61K 9/10* (2013.01); *A61K 31/496* (2013.01); *A61P 25/28* (2018.01)

(58) Field of Classification Search
CPC ...... A61K 9/0043; A61K 9/10; A61K 31/496; A61P 25/28
See application file for complete search history.

(56) References Cited

FOREIGN PATENT DOCUMENTS

| EP | 0 675 126 A1 | 10/1995 | |
|---|---|---|---|
| EP | 0675126 A1 * | 10/1995 | ........... C07D 498/08 |
| WO | WO 95/011248 A1 | 4/1995 | |

OTHER PUBLICATIONS

Khopade et al., Enhanced Brain Uptake of Rifampicin from W/O/W Multiple Emulsions via Nasal Route, Mar.-Apr. 1996, Indian journal of pharmaceutical sciences, vol. 58 iss.2, pp. 83-85. (Year: 1996).*
Walpole et al., The weight of nations: an estimation of adult human biomass, Jun. 18, 2012, BMC public health, vol. 12 iss.1, pp. 1-6. (Year: 2012).*
Iizuka et al., Preventive Effect of Rifampicin on Alzheimer Disease Needs at Least 450 mg Daily for 1 Year: An FDG-PET Follow-Up Study, Jun. 19, 2017, Dementia and Geriatric Cognitive Disorders Extra, vol. 7, pp. 204-214. (Year: 2017).*
Loeb et al., A randomized, controlled trial of doxycycline and rifampin for patients with Alzheimer's disease, Mar. 2004, Journal of the American Geriatric Society, vol. 52 iss. 3, pp. 381-387 (abstract only provided) (Year: 2004).*
English Translation of International Search Report of PCT/JP2018/025512, dated Sep. 4, 2018.
Gomez. Diana et al., 2012 "Intranasal treatment of neurodegenerative diseases and stroke," *Frontiers in Bioscience*, S4: 74-89.
Graff, Candace L. et al., 2003 "P-Glycoprotein Attenuates Brain Uptake of Substrates after Nasal Instillation," *Pharmaceutical Research*, 20, No. 8, pp. 1225-1230.
Khopade A.J. et al., 1996 "Enhanced Brain Uptake of Rifampicin from W/O/W Multiple Emulsions via Nasal Route," *Indian Journal of Pharmaceutical Sciences*, vol. 58, No. 2, pp. 83-85.
Tomiyama, T. et al. 1996 "Inhibition of Amyloid β Protein Aggregation and Neurotoxicity by Rifampicin—Its Possible Function as a Hydroxyl Radical Scavenger," J. Biol Chem, vol. 271, No. 12, p. 6839-6844.
Umeda Tomohiro et al., 2016 "Rifampicin is a candidate preventive medicine against amyloid-β and tau oligomers," *Brain*, vol. 139, Part 5, pp. 1568-1586.
Molloy, D. William, et al., "A multicenter, blinded, randomized, factorial controlled trial of doxycycline and rifampin for treatment of Alzheimer's disease: the DARAD trial," Int J Geriatr Psychiatry May 2013: 28(5): 463-470.

* cited by examiner

*Primary Examiner* — Ali Soroush
(74) *Attorney, Agent, or Firm* — Knobbe, Martens, Olson & Bear, LLP

(57) ABSTRACT

The purpose of the present invention is to provide a dosing technique for rifampicin, the technique being capable of long-term administration by enhancing the direct transfer of rifampicin to the brain and by suppressing the hepatic first-pass effect. This pharmaceutical composition for nasal administration, which contains, as an active ingredient, rifampicins selected from the group consisting of rifampicin, derivatives thereof, and salts thereof, and is used for the prevention or treatment of dementia, is capable of long-term administration by enhancing the direct transfer of rifampicin to the brain and suppressing the hepatic first-pass effect.

7 Claims, 4 Drawing Sheets

FIG. 2

PHARMACEUTICAL COMPOSITION FOR NASAL ADMINISTRATION

TECHNICAL FIELD

The present invention relates to a pharmaceutical composition for nasal administration, that is useful for prevention or treatment of dementia because of having high therapeutic effect and suppressing side effect.

BACKGROUND ART

Dementia includes cerebrovascular dementia developing by a cerebrovascular accident, and degenerative dementia developing by accumulation of abnormal proteins in the brain. The latter dementia includes Alzheimer's disease (AD) in which amyloid β (Aβ) and tau accumulate, frontotemporal dementia (FTD) in which tau or TDP-43 accumulates, and dementia with Lewy bodies (DLB) in which α synuclein accumulates. It is considered that these proteins form oligomers in the brain, and interfere the function of neurons to result in development of the disease. Based on this consideration, as therapeutic drugs for degenerative dementia, development of drugs having the action of suppressing production of these proteins, the action of suppressing formation of oligomers, the action of removing aggregated proteins from the brain and the like is advanced.

For example, for AD, an inhibitor of enzyme (β secretase or γ secretase) involved in production of Aβ, an Aβ vaccine for removing Aβ from the brain, and an Aβ antibody have been developed and subjected to clinical trials. However, most of such development clinically failed for the reasons of appearance of an unexpected side effect, failure in expression of an expected drug efficacy, and the like.

On the other hand, rifampicin that is well known as an antibiotic has been used as oral medicine owing to the antibacterial action thereof. Further, rifampicin is known to have an action of removing free radicals, and as one of such action, involvement in suppression of Aβ aggregation reaction is reported (see Non-patent document 1).

PRIOR ART DOCUMENT

Non-Patent Document

Non-Patent Document 1: Tomiyama, T. and six others, "Inhibition of amyloid beta protein aggregation and neurotoxicity by rifampicin. Its possible function as a hydroxyl radical scavenger.", J Biol Chem, 1996, Vol. 271, p. 6839-6844

SUMMARY OF THE INVENTION

Problems to be Solved by the Invention

The reason of failure in Aβ targeting agents (Aβ producing enzyme inhibitor, Aβ vaccine, Aβ antibody, and so on) in clinical trials targeting AD is considered as too late administration timing aside from the problem of side effect. In other words, removal of Aβ is not worthwhile unless Aβ is removed before development of dementia at which neurons start dying. Therefore, the role of an Aβ targeting agent should lie in prevention rather than in treatment. It has been reported that a tau aggregation inhibitor that first proceeded to clinical trials among tau targeted drugs failed to exert the action of improving the cognitive function in clinical trials that target for AD. Also this result appears to show that administration after development of dementia is too late even with the tau targeted drug.

However, most of the therapeutic drugs that are currently under development have not been developed on the premise of preventive administration, and such drugs face the problems in terms of cost, side effect, administration method and the like. Meanwhile, in administration for preventing dementia, it is necessary to assume a relatively long term as an administration period because the time of development of dementia is unclear.

On the other hand, the present inventor found that rifampicin suppresses formation of oligomers of Aβ, tau, α synuclein in vitro, and that oral administration of rifampicin to AD model mouse in which Aβ accumulates or FTD model mouse in which tau accumulates suppresses accumulation of these protein oligomers in the brain, and leads to recovery of the cognitive function of mouse. The present inventor made investigation setting a goal of practical application of repositioning of oral medicine rifampicin that has been used as an antibiotic, to a dementia prophylactic drug by the use of the action of rifampicin as described above.

In such investigation, however, the present inventor was confronted with the problem that the side effects such as hepatopathy and drug interaction by rifampicin are serious, and this disables long-term administration of rifampicin that is a premise for a prophylactic drug. The drug interaction in this context refers to the phenomenon that the effect of other drug taken simultaneously with rifampicin is attenuated because rifampicin induces cytochrome P450 (CYP) and P-glycoprotein that are involved in drug metabolism in hepatocytes.

Here, orally taken rifampicin is absorbed through the small intestine, and conveyed to the liver through portal vein. Most of the absorbed drug is decomposed and inactivated in the liver, and only a very small part of the administered drug enters the systemic circulation while keeping the activity (this is referred to as the first pass effect). Further, there is a blood-brain barrier (BBB) that restricts exchange of substances, between blood and the brain, so that a very small fraction of rifampicin in the blood enters the brain (about several % to several tens %). In previous administration of rifampicin, it is considered that the brain concentration required for expression of drug efficacy of rifampicin is eventually ensured by taking an adequate amount in which the amount lost in the first pass effect and BBB is preliminarily supplemented. And, it is considered that the side effect of rifampicin occurs when the drug passes through the liver.

In light of the above, it is an object of the present invention to provide a dosing technique of rifampicin allowing long-term administration, by enhancing the direct transfer of rifampicin to the brain, and suppressing the hepatic first-pass effect.

Means for Solving the Problem

As a result of diligent effort, the present inventor found that the above problem is solved by nasally administering rifampicin. The present invention was accomplished by repeating investigations on the basis of the finding.

That is, the present invention provides the invention of the following aspects.

Item 1. A pharmaceutical composition for nasal administration, the pharmaceutical composition containing, as an active ingredient, rifampicins selected from the group consisting of rifampicin, a derivative of rifampicin, and a salt of rifampicin or a rifampicin derivative, for use in prevention or treatment of dementia.

Item 2. The pharmaceutical composition according to item 1, wherein an effective dose of the rifampicins is 0.15 to 3.75 mg/kg/day.

Item 3. The pharmaceutical composition according to item 1 or 2, for use in prevention of dementia.

Item 4. The pharmaceutical composition according to any one of items 1 to 3, wherein the dementia is Alzheimer's disease.

Item 5. Use of rifampicins selected from the group consisting of rifampicin, a derivative of rifampicin, and a salt of rifampicin or a rifampicin derivative, for production of a pharmaceutical composition for nasal administration for prevention or treatment of dementia.

Item 6. A method for treating dementia, the method including nasally administering an effective amount of rifampicins selected from the group consisting of rifampicin, a derivative of rifampicin, and a salt of rifampicin or a rifampicin derivative, to a dementia patient.

Item 7. A method for preventing dementia, the method including nasally administering an effective amount of rifampicins selected from the group consisting of rifampicin, a derivative of rifampicin, and a salt of rifampicin or a rifampicin derivative, to an unaffected subject with high risk of developing dementia.

Advantages of the Invention

According to the pharmaceutical composition of the present invention, a non-invasive, highly effective dosing technique with low side effect that allows long-term administration is provided by preparing rifampicin as a nasal formulation. Therefore, the pharmaceutical composition of the present invention can be applied not only for treatment of dementia but also for prevention of dementia.

BRIEF DESCRIPTION OF THE DRAWINGS

FIG. 2 show the result of immunostaining performed in Test example 1, and shows the effect of rifampicin on Aβ oligomers or synaptophysin.

EMBODIMENTS OF THE INVENTION

Figure 1:
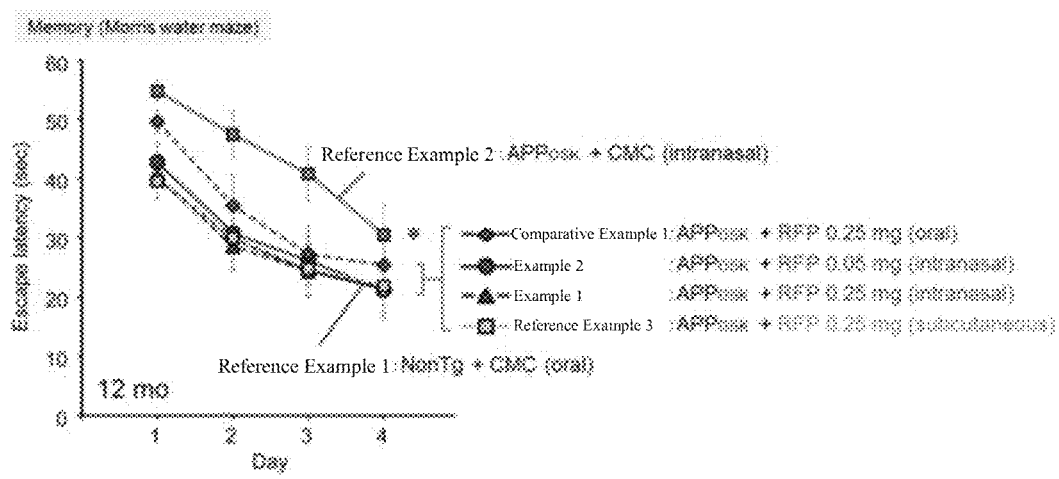
FIG. 1 shows the result of the behavior test performed in Test example 1, and shows the effect of rifampicin administration on the murine cognitive function.

The pharmaceutical composition of the present invention contains, as an active ingredient, rifampicins selected from the group consisting of rifampicin, a derivative of rifampicin, and a salt of rifampicin or a rifampicin derivative, and is used for prevention or treatment of dementia, and is nasally administered.

[Rifampicins]

The pharmaceutical composition of the present invention contains, as an active ingredient, rifampicins selected from the group consisting of rifampicin, a derivative of rifampicin, and a salt of rifampicin or a rifampicin derivative. Rifampicins have the action of suppressing formation of oligomers of amyloid β, tau, and α synuclein that are causative proteins of degenerative dementia such as Alzheimer's disease, frontotemporal dementia, and dementia with Lewy bodies. Rifampicins have a naphthydroquinone or naphtquinone structure, and this structure is considered to contribute to the action of rifampicin as a free radical scavenger.

Rifampicin is generally a compound represented by the following formula (I).

[Chemical 1]

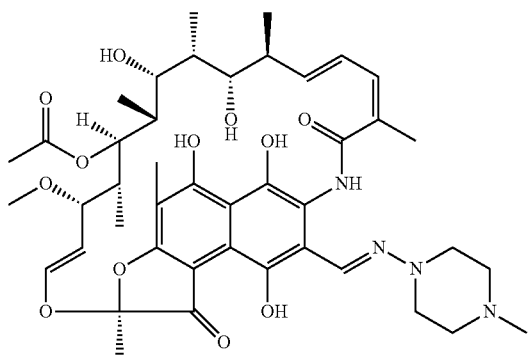

(I)

Derivatives of rifampicin are not particularly limited as long as they have a naphthydroquinone or naphtquinone structure, and are pharmaceutically acceptable, and examples of the rifampicin derivatives include 3-Folmyl-Rifamycin SV, Rifamysin S, Rifamycin B, Rifamycin SV, and 25-Desacetyl-RFP which is a main active metabolite. Among the rifampicin derivatives, a derivative not having a substituent at the 3 position of the 1,4-dihydroxynaphthalene structure responsible for the antibiotic activity, for example, Rifamycin SV is preferred from the viewpoint of suppressing induction of resistant bacteria due to long-term administration. These rifampicin derivatives may be used singly or in combination of two or more kinds.

A salt of rifampicin is not particularly limited as long as it forms a salt with rifampicin or a rifampicin derivative, and is pharmaceutically acceptable. Examples of the salt of rifampicin include alkali metal (potassium, sodium, and so on) salts, alkali earth metal (calcium, magnesium, and so on) salts, ammonium salts, pharmaceutically acceptable organic amine (tetramethylammonium, triethylamine, methylamine, dimethylamine, cyclopentylamine, benzylamine, phenethylamine, piperidine, monoethanolamine, diethanolamine, tris (hydroxymethyl)aminomethane, lysine, arginine, N-methyl-D-glucamine, and so on) salts, inorganic acid salts (hydrochloride, hydrobromate, hydroiodide, sulfate, phosphate, nitrate, and so on), and organic acid salts (acetate, lactate, tartrate, benzoate, citrate, methanesulfonate, ethanesulfonate, benzenesulfonate, toluenesulfonate, isethionate, glucuronate, gluconate, and so on). These salts may be used singly or in combination of two or more kinds.

As the rifampicins, one kind or a combination of two or more kinds selected from rifampicin, a salt of rifampicin, a derivative of rifampicin, a salt of a derivative of rifampicin may be used.

Among the above-described rifampicins, rifampicin and Rifamycin SV are preferred.

[Formulation]

The pharmaceutical composition of the present invention is prepared as a nasal formulation. The nasal formulation is formulated to contain the above-described rifampicins as an active ingredient, by a measure well known per se, and may appropriately contain a pharmaceutically acceptable base and/or additive.

Examples of the pharmaceutically acceptable base and/or additive include a diluent, a thickening agent, a lubricant, a binder, a disintegrator, a solvent, a solubilizing agent, a suspending agent, an emulsifier, an isotonizing agent, a buffer, a soothing agent, and a stabilizer. Also, additives such as a preservative (antiseptic), a pH regulator, a refrigerant, an antioxidant, a humectant, an agglutinant, and a flavoring agent may be contained as is necessary.

Examples of the diluent include lactose, white sugar, D-mannitol, starch, corn starch, crystalline cellulose, and light anhydrous silicic acid. Examples of the thickening agent include polyhydric alcohols such as glycerin, and macrogol, celluloses such as methylcellulose, carboxymethylcellulose, and hydroxypropylmethylcellulose, hydrophilic polymers such as polyvinyl alcohol, polyvinyl pyrrolidone, carboxyvinyl polymer, sodium carboxymethylcellulose, methylcellulose, hydroxymethylcellulose, hydroxyethylcellulose, and hydroxypropylcellulose, sodium alginate, chondroitin sulfate, cyclodextrin, d-α-tocopherylpolyethylene glycol 1000 succinate, and polyethylene glycol. Examples of the lubricant include magnesium stearate, calcium stearate, talc, and colloidal silica. Examples of the binder include crystalline cellulose, white sugar, D-mannitol, dextrin, hydroxypropylcellulose, hydroxypropylmethylcellulose, polyvinyl pyrrolidone, starch, sucrose, gelatin, methylcellulose, and sodium carboxymethylcellulose. Examples of the disintegrator include starch, carboxymethylcellulose, calcium carboxymethylcellulose, croscarmellose sodium, sodium carboxymethyl starch, and L-hydroxypropylcellulose. Examples of the solvent include water, ethanol, isopropyl alcohol, acetone, propylene glycol, macrogol, sesame oil, and corn oil. Examples of the solubilizing agent include celluloses such as methylcellulose, carboxymethylcellulose, and hydroxypropylmethylcellulose; polyethylene glycol, propylene glycol, D-mannitol, benzyl benzoate, ethanol, trisaminomethane, cholesterol, triethanolamine, sodium carbonate, sodium citrate, polyvinyl pyrrolidone, and macrogol. Examples of the suspending agent include surfactants such as stearyltriethanolamine, sodium lauryl sulfate, laurylaminopropionic acid, lecithin, benzalkonium chloride, benzethonium chloride, glyceryl monostearate, polyoxyethylene hydrogenated castor oil, and polysorbate, polyhydric alcohols such as glycerin, and macrogol, saccharides such as sorbitol, mannitol, and sucrose, celluloses such as methylcellulose, carboxymethylcellulose, and hydroxypropylmethylcellulose, hydrophilic polymers such as polyvinyl alcohol, polyvinyl pyrrolidone, carboxyvinyl polymer, sodium carboxymethylcellulose, methylcellulose, hydroxymethylcellulose, hydroxyethylcellulose, and hydroxypropylcellulose, and chondroitin sulfate. Examples of the isotonizing agent include glucose, D-sorbitol, sodium chloride, glycerin, D-mannitol, potassium chloride, concentrated glycerin, propylene glycol, and sucrose. Examples of the buffer include phosphates (dibasic sodium phosphate, sodium dihydrogenphosphate, and so on), boric acid, borax, acetates (sodium acetate and so on), carbonates (sodium carbonate, calcium carbonate, potassium carbonate, and so on), citric acid, and sodium L-glutamate. Examples of the soothing agent include benzyl alcohol, chlorobutanol, propylene glycol, ethyl aminobenzoate, and lidocaine. Examples of the stabilizer include sulfur compounds such as sodium sulfite, sodium hydrogen sulfite, sodium metabisulfite, sodium thiosulfate, Rongalite, thioglycerol, thioglycollic acid, thiolactic acid, cysteine, glutathione, thioacetic acid, methionine, thiosorbitol, thioglucose, and thiourea, inorganic acids and salts thereof such as boric acid, borax, phosphoric acid, metaphosphoric acid, sodium carbonate, and sodium hydrogencarbonate, organic acids such as formic acid, oxalic acid, tartaric acid, citric acid, and edetic acid, and salts thereof (such as disodium edetate), acid amides such as acetamide, diethylacetamide, nicotinamide, urea, and barbital, urea derivatives, polyhydric alcohols and saccharides such as glycol, propylene glycol, glycerin, polyethylene glycol, glucose, and ascorbic acid, phenols such as phenol, thymol, quinone, coumarone, and isocoumarone, dibutylhydroxytoluene, and amino acids and proteins such as glycine, glutamic acid, lysine, phenylalanine, casein, and edestin. Examples of the emulsifier include glycerin ester (glyceryl monooleate), saponin (Enju saponin, Quillaia extract, soybean saponin, and so on), sucrose fatty acid esters, lecithin (vegetable lecithin, yolk lecithin, soybean lecithin, and so on), polyhydric alcohols (oleyl alcohol, stearyl alcohol, cetyl alcohol, and so on), fat ester (such as octyldodecyl myristate), medium-chain fatty acid triglyceride (MCT), various surfactants (alkylbenzene sulfonate type emulsifier, benzalkonium chloride, sorbitan sesquioleate, dodecylbenzenesulfonic acid, and so on), and triethanolamine. Examples of the preservative (antiseptic agent) include p-hydroxybenzoates such as propyl p-hydroxybenzoate, and butyl p-hydroxybenzoate, parabens such as methylparaben, ethylparaben, propylparaben, and butylparaben, invert soaps such as benzalkonium chloride, benzethonium chloride, chlorhexidine gluconate solution, and cetylpyridinium chloride, alcohol derivatives such as chlorobutanol, benzyl alcohol, and phenethyl alcohol, organic acids and salts thereof such as sodium dehydroacetate, sorbic acid, and sodium sorbate, and phenols such as p-chloromethoxyphenol, and p-chlorometacresol. Examples of the pH regulator include sodium hydroxide, potassium hydroxide, trisodium phosphate, disodium hydrogenphosphate, hydrochloric acid, nitric acid, citric acid, boric acid, and acetic acid. Examples of the refrigerant include l-menthol, camphor, and mentha water. Examples of the antioxidant include sulfite, ascorbic acid, citric acid, and disodium edetate. Examples of the humectant include propylene glycol, polysorbate, macrogol, and glycerin. Examples of the agglutinant include hydroxypropylcellulose, hydroxypropylmethylcellulose 2208, carboxyvinylpolymer, propyleneglycol, and polysorbate 80. Examples of the flavoring agent include trehalose, malic acid, maltose, potassium gluconate, anise essential oil, vanilla essential oil, cardamon essential oil, and crude drug components.

The pharmaceutical composition of the present invention may be a liquid formulation or a solid formulation, with the liquid formulation being preferred. A liquid formulation can be produced by mixing rifampicins, with a solvent, a solubilizing agent, a suspending agent, an isotonizing agent, a buffer, a soothing agent, and so on, as necessary, to dissolve, suspend or emulsify the rifampicins. It is also preferred to further add a thickening agent to improve the viscosity and impart the retentivity. A solid formulation can be produced by uniformly mingling rifampicins, with a diluent, a binder, a disintegrator, or other appropriate additive, and obtaining granules by an appropriate granulation method, and further drying as necessary to make the granules into powder or microgranules.

In the pharmaceutical composition of the present invention, the content of rifampicin is not particularly limited as long as it is prepared as a nasal formulation, and is appropriately adjusted so that rifampicin is administered in the later-described dosage. For example, a content of rifampicin in the pharmaceutical composition of the present invention can be 0.4 w/v % or more, preferably 0.5 w/v % or more. Further, from the viewpoint of effectively administering an effective amount at a few frequency of administration, the content of rifampicin in the pharmaceutical composition of the present invention may be 2 w/v % or more, 2.5 w/v % or more, 5 w/v % or more, or 30 w/v % or more. Further, the content of rifampicin in the pharmaceutical composition of the present invention can be 95 w/v % or less, and from the viewpoint of obtaining the sprayability of the nasal formulation, the content of rifampicin can be 85 w/v % or less, or 50 w/v % or less. Specific ranges of the content of rifampicin in the pharmaceutical composition of the present invention can be, for example, 0.4 to 95 w/v %, 0.4 to 85 w/v %, 0.4 to 50 w/v %, 0.5 to 95 w/v %, 0.5 to 85 w/v %, 0.5 to 50 w/v %, 2 to 95 w/v %, 2 to 85 w/v %, 2 to 50 w/v %, 2.5 to 95 w/v %, 2.5 to 85 w/v %, 2.5 to 50 w/v %, 5 to 95 w/v %, 5 to 85 w/v %, 5 to 50 w/v %, 30 to 95 w/v %, 30 to 85 w/v %, 30 to 50 w/v %.

The pharmaceutical composition of the present invention may be packed in a container for nasal administration before use. As the container for nasal administration, a commercially available one can be appropriately used.

[Dosage and Administration]

Since the pharmaceutical composition of the present invention is prepared for nasal administration, it provides drug efficacy of higher than or equivalent to that of the oral administration with a smaller dosage compared with that in oral administration and can reduce the side effect of the hepatopathy. Therefore, the pharmaceutical composition of the present invention can be repetitively administered for a long term in a dosage smaller than that in the case of being orally administered as an antibiotic.

The effective dose of rifampicin of the pharmaceutical composition of the present invention to human is, for example, 1/50 or more, preferably 1/25 or more, more preferably 1/10 or more, further preferably 1/7.5 or more, relative to the dosage when rifampicin is orally administered as an antibiotic (for example, 7.5 to 10 mg/kg/day) from the viewpoint of expression of drug efficacy, and is, for example, 1/2 or less, preferably 1/3 or less, more preferably 1/3.75 or less, relative to the dosage when rifampicin is orally administered as an antibiotic (for example, 7.5 to 10 mg/kg/day) from the viewpoint of suppressing side effect. A specific range of the effective dose of rifampicin to human is, for example, 1/50 to 1/2, 1/50 to 1/3, 1/50 to 1/3.75, 1/25 to 1/2, 1/25 to 1/3, 1/25 to 1/3.75, 1/10 to 1/2, 1/10 to 1/3, 1/10 to 1/3.75, 1/7.5 to 1/2, 1/7.5 to 1/3, 1/7.5 to 1/3.75, particularly, for example, 1/50 or more and 1/2 or less, preferably 1/25 or more and 1/3 or less, more preferably 1/10 or more and 1/3 or less, further preferably 1/7.5 or more and 1/3.75 or less, relative to the dosage when rifampicin is orally administered as an antibiotic (for example, 7.5 to 10 mg/kg/day).

A more specific effective dose of rifampicin of the pharmaceutical composition of the present invention is, for example, 0.15 mg/kg/day or more, preferably 0.3 mg/kg/day or more, more preferably 0.75 mg/kg/day or more, further preferably 1 mg/kg/day or more from the viewpoint of expression of drug efficacy, and is, for example, 3.75 mg/kg/day or less, preferably 2.5 mg/kg/day or less, more preferably 2 mg/kg/day or less from the viewpoint of suppressing side effect. A specific range of the effective dose of rifampicin of the pharmaceutical composition of the present invention is 0.15 to 3.75 mg/kg/day, 0.15 to 2.5 mg/kg/day, 0.15 to 2 mg/kg/day, 0.3 to 3.75 mg/kg/day, 0.3 to 2.5 mg/kg/day, 0.3 to 2 mg/kg/day, 0.75 to 3.75 mg/kg/day, 0.75 to 2.5 mg/kg/day, 0.75 to 2 mg/kg/day, 1 to 3.75 mg/kg/day, 1 to 2.5 mg/kg/day, 1 to 2 mg/kg/day, particularly, for example, 0.15 to 3.75 mg/kg/day, preferably 0.3 to 2.5 mg/kg/day, more preferably 0.75 to 2.5 mg/kg/day, further preferably 1 to 2 mg/kg/day (especially 1.67 mg/kg/day).

The pharmaceutical composition of the present invention is suited for repetitive administration because it can be administered in a small dosage. Therefore, the pharmaceutical composition of the present invention can be administered for a long term. For example, the pharmaceutical composition of the present invention can be administered over 6 months or more, for example, over 6 months to 3 years. The administration interval may be every other day, or once to twice a week.

[Administration Target]

The pharmaceutical composition of the present invention can be used for prevention of dementia and for treatment of dementia. Preferably, the pharmaceutical composition of the present invention can be used for prevention of dementia. Examples of dementia include degenerative dementia and cerebrovascular dementia, and degenerative dementia is preferred. Examples of degenerative dementia include dementia that develops by accumulation of dementia causative protein such as amyloid β (Aβ), tau, TDP-43, or α synuclein, and concrete examples include Alzheimer's disease (AD) in which amyloid β (Aβ) and tau accumulate, frontotemporal dementia (FTD) in which tau or TDP-43 accumulates, and dementia with Lewy bodies (DLB) in which α synuclein accumulates, and Alzheimer's disease (AD) is preferred.

When the pharmaceutical composition of the present invention is used for prevention of dementia, the administration target is not particularly limited as long as the target is an unaffected subject with high risk of developing dementia. Examples of the unaffected subject with high risk of developing dementia include a senile plaque-positive normal healthy person, and a family member of a family line of familial Alzheimer's disease. When the pharmaceutical composition of the present invention is used for treatment of dementia, the administration target is not particularly limited as long as the target is a patient diagnosed as dementia, and in need of stopping progression of the symptom of dementia.

[Pharmacological Action]

Dendrites of olfactory neuron reach the nasal mucosa of the upper part of the nose, and the smell information obtained at the olfactory receptor on the cell surface is sent to the olfactory bulb of the brain through the axon of the neuron. There is no blood-brain barrier (BBB) between the nasal mucosa and the olfactory neuron. In the vicinity of the axon bundle of the olfactory neuron, there is cerebrospinal fluid, however, there is no blood-cerebrospinal fluid barrier (BCSFB) that inhibits exchange of a substance between the blood and the cerebrospinal fluid. Therefore, the active ingredient, rifampicins, that have reached the nasal mucosa by nasal administration of the pharmaceutical composition of the present invention are taken in the olfactory neuron or the cerebrospinal fluid without being hindered by BBB and BCSFB, and can migrate into the brain.

Thus, according to the pharmaceutical composition of the present invention, the direct transfer of rifampicins to the brain is improved, so that the hepatic first-pass effect can be suppressed. Therefore, the pharmaceutical composition of the present invention achieves high drug efficacy due to improved direct transfer to the brain, and low side effect due to suppression of the hepatic first-pass effect, as well as being non-invasive in terms of the administration form.

Rifampicins having reached the brain bring about suppression of formation or aggregation of oligomers of dementia causative proteins such as amyloid β (Aβ), tau, TDP-43, and α synuclein, or disappearance of formed or aggregated oligomers of the dementia causative proteins in the case of degenerative dementia. This results in delay of development of dementia, or amelioration of symptoms of dementia (for example, recovery of disturbance of memory owing to regeneration of synapse). In the case of cerebrovascular dementia, rifampicins having reached the brain ameliorate cerebrovascular disease by the neuroprotective action via the radical scavenger action. This brings about amelioration in symptoms of dementia.

Examples

Hereinafter, the present invention will be described more specifically by showing examples, however, the present invention is not limited to these examples Test Example In the present test example, an administration composition containing or not containing rifampicin was administered to the mouse shown in Table 1 everyday over 1 month in the dosage and administration shown in Table 1.
(Administration Target)
Male APP $_{OSK}$ mice (Tomiyama et al. J Neurosci. 2010; 30:4845-56) aged 11 months were prepared. APP $_{OSK}$ mice weigh about 30 g. The 60 APP $_{OSK}$ mice were classified into five groups A to E, each containing 12 mice. Separately, 12 wild-type mice (non-Tg littermate) of the same age in month were prepared. It is to be noted that APP $_{OSK}$ mouse is an amyloid precursor protein (APP) transgenic mouse (Alzheimer's disease model), and shows accumulation of amyloid β (Aβ) protein.
(Administration Composition)
In a 0.5 w/v % carboxymethylcellulose (CMC; Sigma-Aldrich, Carboxymethylcellulose sodium salt low viscosity, C5678) solution, a rifampicin drug (RFP; Sigma-Aldrich, Rifampicin ≥97% (HPLC), powder, another name: 3-(4-methylpiperazinyliminomethyl)rifamycin SV, rifamycin AMP, rifampicin, R3501) was suspended in an amount that is to be the dosage shown in Comparative Example 1, Examples 1 to 2, and Reference Example 3 in Table 1 to prepare an administration composition.
(Administration Method)
Administration was performed without anesthesia using a rodent oral sonte for oral administration, a Pipetman (white tip) for nasal administration, and an injection syringe for subcutaneous administration.

TABLE 1

|  | Reference Example 1 | Reference Example 2 | Comparative Example 1 | Example 1 | Example 2 | Reference Example 3 |
|---|---|---|---|---|---|---|
| Dosage per day | 300 μl CMC | 10 μl CMC | RFP 0.25 mg/ 300 μl CMC | RFP 0.25 mg/ 10 μl CMC | RFP 0.05 mg/ 10 μl CMC | RFP 0.25 mg/ 300 μl CMC |
| Administration | Oral | Nasal | Oral | Nasal | Nasal | Subcutaneous |
| Administration target | Non-Tg (Wild-type) | APPosk | APPosk | APPosk | APPosk | APPosk |

(Result 1—Behavior Test)
Mice after completion of administration (aged 12 months) were subjected to a behavior test, and the effect of rifampicin on the murine cognitive function was compared. The behavior test was performed by measuring space reference memory of mouse using a Morris water maze according to the method of Umeda et al. Brain 2016; 139:1568-86. The mice subjected to the behavior test were 12 mice (Comparative Example 1, Example 1, Example 2), and 11 mice (Reference Example 1, Reference Example 2, Reference Example 3) excluding the mouse that died during the administration period.

The result of the behavior test is shown in FIG. 1. In any of the oral administration (oral), nasal administration (intranasal), and subcutaneous administration (subcutaneous), amelioration of disturbance of memory of APP OSK mouse was confirmed. However, the ameliorating effect was imperfect by oral administration (Comparative Example 1). In contrast to this, the ameliorating effect reached to the same level as in wild-type mouse by nasal administration (Example 1 and Example 2) and by subcutaneous administration (Reference Example 3). It was also confirmed that the ameliorating effect by nasal administration was higher than the case of oral administration (Comparative Example 1) even when the dosage decreased to one-fifth (0.05 mg/day) (Example 2).
(Result 2—Impaired Liver Function)
Blood was sampled from mice after end of the behavior test, and serum was separated from the blood to prepare a serum sample. Hepatic enzymes AST (GOT) and ALT (GPT) in the serum sample were measured, and the degree of impaired liver function by rifampicin was compared.

Measurement results of hepatic enzymes are shown in Table 2. In comparison with CMC-administered APP $_{OSK}$ mouse (Reference Example 2), significant elevation of AST that suggests hepatotoxicity was observed in RFP-orally administered mouse (Comparative Example 1). In contrast to this, elevation as in Comparative Example 1 was not observed in the nasally administered mouse (Example 1, Example 2). Slight elevation of AST in the nasally administered mouse (Example 1, Example 2) is attributable to that part of the intranasally administered drug flows toward the throat, and is absorbed through the small intestine. Unlike the nasal administration in mouse, it is considered that such accidental swallowing little occurs in nasal administration in human. In the subcutaneous administration (Reference Example 3), elevation of AST was not observed. Regarding ALT, no significant change was observed in any administration method.

TABLE 2

| | Reference Example 1 | Reference Example 2 | Comparative Example 1 | Example 1 | Example 2 | Reference Example 3 |
|---|---|---|---|---|---|---|
| | | | | APPosk | | |
| | Non-Tg | | Rifampicin (mg/day) | | | |
| | CMC Oral n = 10 | CMC Nasal n = 9 | 0.25 Oral n = 12 | 0.25 Nasal n = 12 | 0.05 Nasal n = 11 | 0.25 Subcutaneous n = 10 |
| AST | 74 ± 5 | 104 ± 13 | 248 ± 56* | 189 ± 25 | 165 ± 32 | 72 ± 6 |
| ALT | 29 ± 1 | 35 ± 3 | 39 ± 5 | 45 ± 5 | 40 ± 10 | 29 ± 2 |

Values of AST and ALT are indicated by Mean ± SEM (IU/L).
*The p value of difference between groups of AST values of Non-Tg mouse, CMC-administered Tg mouse and subcutaneously administered Tg mouse was less than 0.06.
In Ca57BL6 mouse, the normal value of AST was 68 ± 24, and the normal value of ALT was 30 ± 8.

(Result 3—Immunohistological Staining)

Brains were removed from mice after end of the behavior test, and the effects of rifampicin on Aβ oligomers, synaptophysin, and phosphorylated tau were compared by means of immunohistological staining.

According to the procedure described in Umeda et al. Brain 2016; 139:1568-86, Aβ oligomers (Aβ oligomers are considered to cause phosphorylation of tau and reduction in synaptophysin), synaptophysin (marker protein of synapse), and phosphorylated tau were stained by immunohistological staining. For staining Aβ oligomers, 11A1 antibody (available from Immune-Biological laboratories Co., Ltd.) was used, and for staining synaptophysin, SVP-38 antibody (available from Sigma) was used. Mouse monoclonal PHF-1 antibody (anti p-Ser396/404-tau antibody, provided by Dr. Peter Davies, Albert Einstein College of Medicine) was used for staining phosphorylated tau. After staining, Aβ oligomers, synaptophysin, and phosphorylated tau were quantified by using NIH image-J.

Figure 2:
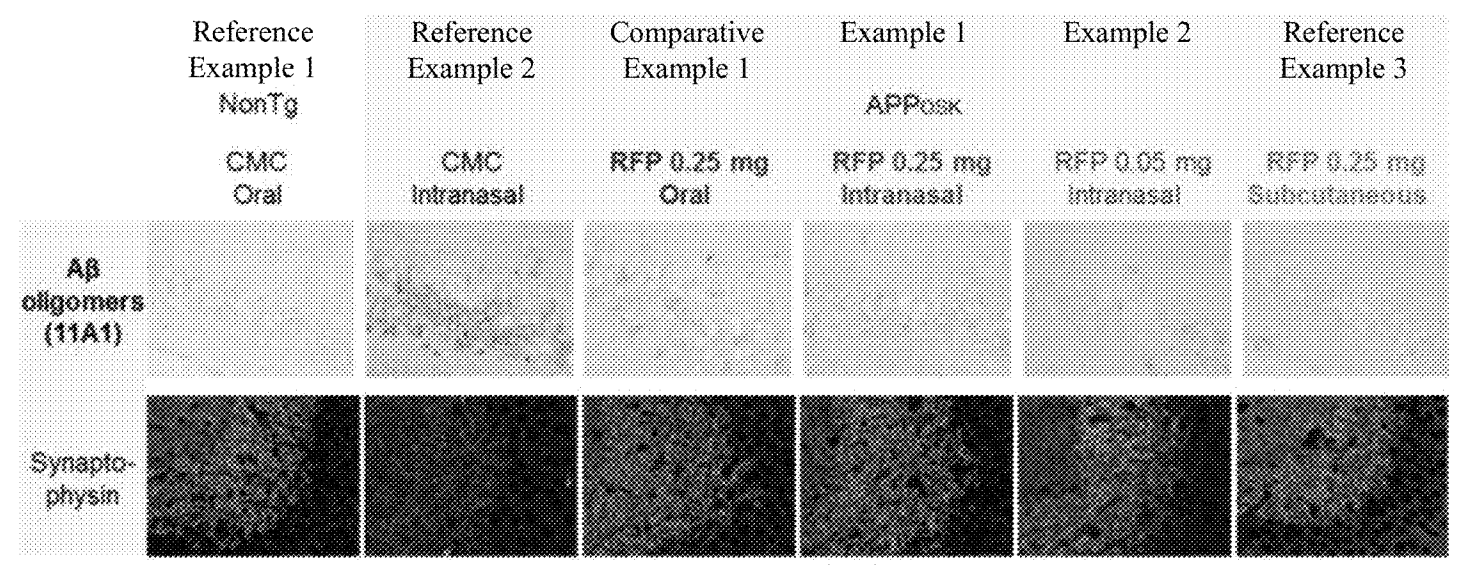

FIG. 2 shows photographs of tissues of immunostained oligomers (Aβ oligomers) and synaptophysin (Synaptophysin). In FIG. 2, the upper section shows hippocampus CA3 tissues, and the lower section shows hippocampus CA2/3 tissues. In any of the oral administration (Comparative Example 1), nasal administration (Example 1, Example 2), and subcutaneous administration (Reference Example 3) of RFP, Aβ oligomer having accumulated in the brain reduced, and the synaptophysin having reduced was recovered.

Figure 3:
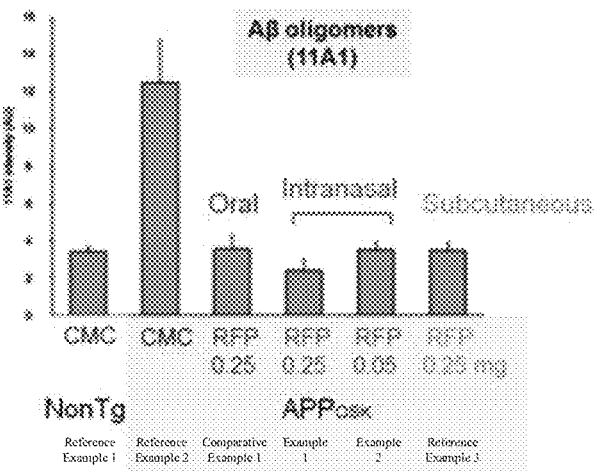
FIG. 3 shows the result of quantification of Aβ oligomers on the basis of the immunostaining of FIG. 2.

FIG. 3 shows the result of quantification of Aβ oligomers obtained from the result of immunostaining of FIG. 2. In any of the oral administration (Comparative Example 1), nasal administration (Example 1, Example 2), and subcutaneous administration (Reference Example 3) of RFP, Aβ oligomers reduced to at least the same level as that in wild-type mouse (Reference Example 1). Especially in comparison for the same dosage, the effect of reducing Aβ oligomers was the highest in the nasal administration (Example 1).

Figure 4:
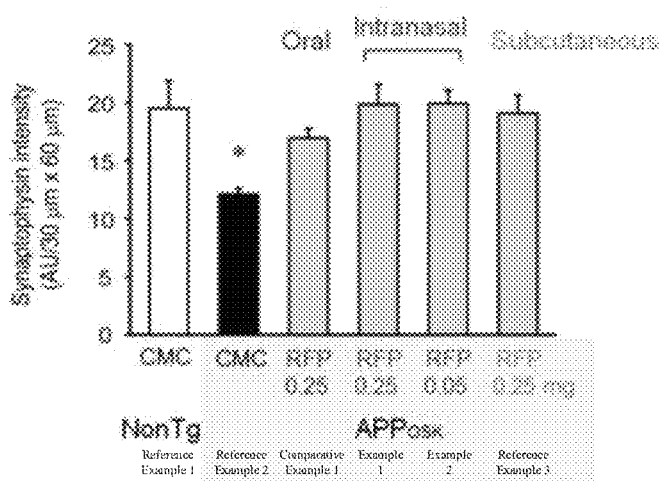
FIG. 4 shows the result of quantification of synaptophysin on the basis of the immunostaining of FIG. 2.

FIG. 4 shows the result of quantification of synaptophysin obtained from the result of immunostaining of FIG. 2.

In any of the oral administration (Comparative Example 1), nasal administration (Example 1, Example 2), and subcutaneous administration (Reference Example 3) of RFP, synaptophysin of hippocampus showed the tendency of recovering. In particular, the effect by the oral administration (Comparative Example 1) was weak. On the other hand, by the nasal administration (Example 1, Example 2) or subcutaneous administration (Reference Example 3), the recovery to the same level as that in wild-type mouse (Reference Example 1) was observed. Likewise the result of the behavior test, it was also confirmed that the effect by the nasal administration was higher than that by the oral administration (Comparative Example 1) even when the dosage decreased to one-fifth (0.05 mg/day) (Example 2).

Figure 5:
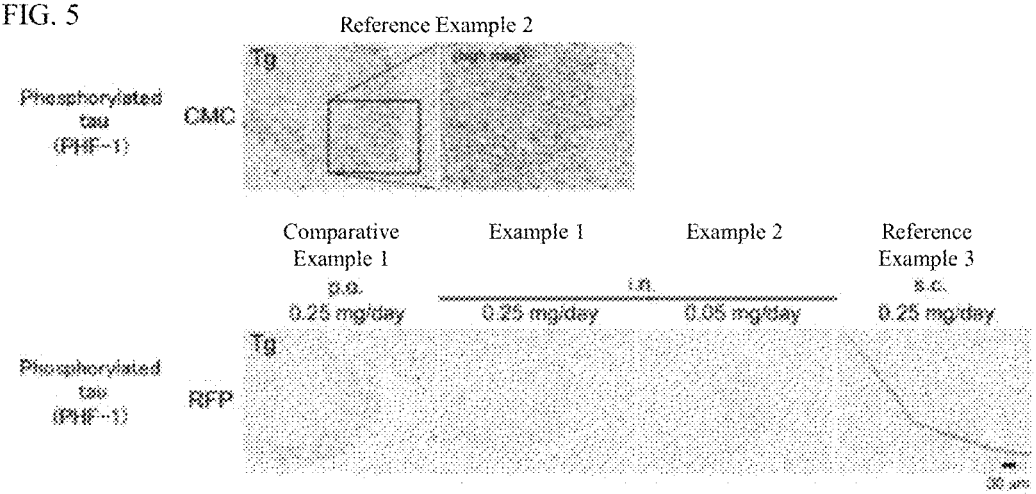
FIG. 5 show the result of immunostaining performed in Test example 1, and shows the effect of rifampicin on phosphorylated tau.

FIG. 5 shows photographs of tissues after immunostaining of phosphorylated tau. FIG. 5 shows hippocampus CA2/3 tissue. In any of the oral administration (Comparative Example 1), nasal administration (Example 1, Example 2), and subcutaneous administration (Reference Example 3) of RFP, phosphorylated tau having accumulated in the brain reduced.

Figure 6:
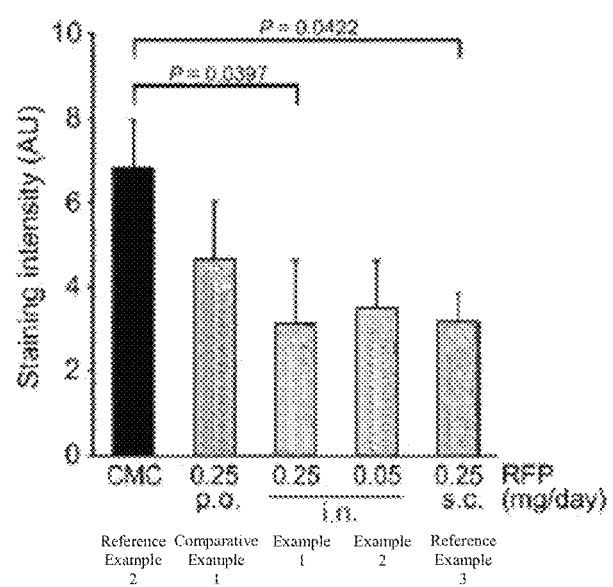
FIG. 6 shows the result of quantification of phosphorylated tau on the basis of the immunostaining of FIG. 5.

FIG. 6 shows the result of quantification of phosphorylated tau obtained from the result of immunostaining of FIG. 5. In any of the oral administration (Comparative Example 1), nasal administration (Example 1, Example 2), and subcutaneous administration (Reference Example 3) of RFP, phosphorylated tau of hippocampus showed the tendency of reducing. In particular, the effect was weak by the oral administration (Comparative Example 1), and on the other hand, the effect was high by the nasal administration (Example 1, Example 2) or subcutaneous administration (Reference Example 3). Further, in comparison for the same dosage, the effect of reducing phosphorylated tau was the highest in the nasal administration (Example 1).

These results demonstrated that in administration of rifampicin, nasal administration is superior to oral administration in the point that the drug efficacy is high and the side effect is low, and also nasal administration is superior to subcutaneous administration in that it is no-invasive. The administration period of 1 month for mouse that brought such an effect corresponds to about 3.3 years in human. Therefore, the results revealed that nasal administration of rifampicin is suited not only for treatment of dementia but also for prevention of dementia because nasal administration of rifampicin is suited for long-term administration. In the present example, effective doses of 0.05 mg/animal/day (1.67 mg/kg/day) and 0.25 mg/animal/day (8.33 mg/kg/day) as nasal doses for mouse (body weight: about 30 g) were shown, and from the obtained result, the effect is expected only with a dose of about 10% of these doses. Also, it is considered that administration of longer term is possible, the effect is expected even with a still lower dose (for example, 0.15 mg/kg/day) in consideration of such long-term administration. Meanwhile, considering that the oral dose of rifampicin to human is prescribed to be 450 to 600 mg/60 kg/day (7.5 to 10 mg/kg/day), and that the effect is exhibited in nasal administration even with a small amount of one-fifth that of oral administration, a half of conventional dose (for example, 3.75 mg/kg/day) would naturally effective in administration to human. Accordingly, in administration to human, the effective dose may be 0.15 to 3.75 mg/kg/day.

The invention claimed is:

1. A method of treating a subject to reduce development of dementia in the subject, the method comprising:

nasally administering to the subject a pharmaceutical composition comprising, as an active ingredient, a rifampicin selected from the group consisting of rifampicin, a derivative of rifampicin, and a salt of rifampicin or a rifampicin derivative, wherein a dose of the rifampicin, the derivative of rifampicin or the salt of the rifampicin or the rifampicin derivative is 2 mg/kg/day or less.

2. The method of claim 1, wherein the pharmaceutical composition is a liquid formulation in which the rifampicin is dissolved or suspended, or a powder or granular solid formulation containing the rifampicin.

3. The method according to claim 1, wherein the dementia is Alzheimer's disease.

4. The method according to claim 2, wherein the dementia is Alzheimer's disease.

5. The method of claim 1, wherein the pharmaceutical composition is administered over 6 months or more.

6. The method of claim 1, wherein the pharmaceutical composition is administered over 6 months to 3 years.

7. The method of claim 1, wherein the pharmaceutical composition is administered every other day, or once to twice a week.

* * * * *